United States Patent [19]

Carrington et al.

[11] Patent Number: 5,766,885
[45] Date of Patent: *Jun. 16, 1998

[54] POTYVIRUS VECTORS FOR THE EXPRESSION OF FOREIGN GENES

[75] Inventors: James C. Carrington, College Station, Tex.; Valerian V. Dolja, Corvallis, Oreg.

[73] Assignee: Texas A & M University, College Station, Tex.

[*] Notice: The term of this patent shall not extend beyond the expiration date of Pat. No. 5,491,076.

[21] Appl. No.: 468,067

[22] Filed: Jun. 6, 1995

Related U.S. Application Data

[63] Continuation-in-part of Ser. No. 146,881, Nov. 1, 1993, Pat. No. 5,491,076.

[51] Int. Cl.$^6$ .............. C12N 7/01; C12N 15/01; C12P 21/00
[52] U.S. Cl. .......... 435/70.1; 435/69.1; 435/69.4; 435/69.52; 435/69.6; 435/91.1; 435/91.33; 435/410; 435/419
[58] Field of Search .................. 435/172.3, 69.4, 435/69.52, 69.1, 69.6, 70.1, 91.1, 91.33, 240.1, 240.4, 320.1, 410, 419; 935/6, 11, 22–25, 47, 51, 67

[56] References Cited

U.S. PATENT DOCUMENTS

| | | | |
|---|---|---|---|
| 4,855,237 | 8/1989 | Morinaga | 435/320 |
| 4,874,702 | 10/1989 | Fiers | 435/172 |
| 4,874,703 | 10/1989 | Jaskunas | 435/252.33 |
| 5,162,601 | 11/1992 | Slightom | 800/205 |

FOREIGN PATENT DOCUMENTS

| | | |
|---|---|---|
| 67553 | 12/1982 | European Pat. Off. . |
| 194809 | 9/1986 | European Pat. Off. . |
| 278667 | 2/1988 | European Pat. Off. . |
| 8706261 | 10/1987 | WIPO . |
| 9303161 | 2/1993 | WIPO . |

OTHER PUBLICATIONS

Dolja, V.V., et al., *Proc. Natl. Acad. Sci.*, 89:10208–10212 (1992).
Dolja, V.V. et al., *J. Virol.*, 67(10):5968–5875 (1993).
Donson, et al. *Proc. Natl. Acad. Sci. USA* 88:7204–7208 (1991).
Carrington J.C. et al. *J. Virol.* 67(12):6995–7000 (1993).
Carrington J.C. et al. *J. Virol.* 64(4):1590–1597 (1990).
R.E.F. Matthews (1991) In: *Plant Virology* , 3$^{rd}$. ed., Academic Press, San Diego, CA, pp. 486–487.

*Primary Examiner*—Douglas W. Robinson
*Assistant Examiner*—Elizabeth F. McElwain
*Attorney, Agent, or Firm*—Baker & Botts, L.L.P.

[57] ABSTRACT

The present invention provides an expression vector adapted for expressing heterologous proteins in plants susceptible to a polyprotein-producing plant virus. The vector utilizes the unique ability of viral polyprotein proteases to cleave heterologous proteins from viral polyproteins. Also provided is a method for expressing heterologous proteins in plants using these unique expression vectors.

9 Claims, 9 Drawing Sheets

POTYVIRUS VECTORS FOR THE EXPRESSION OF FOREIGN GENES

CROSS-REFERENCE TO RELATED APPLICATION

This application is a continuation-in-part of application Ser. No. 08/146,881, filed Nov. 1, 1993, now U.S. Pat. No. 5,491,076, which is incorporated herein by reference.

BACKGROUND OF THE INVENTION

1. Field of the Invention

The present invention relates to polyprotein-producing viral vectors for production of non-native proteins and which employ proteolytic digestion of the non-native proteins by the viral vector's own proteases.

2. Description of Related Art

Recombinant DNA techniques and genetic technologies have led to progress in the development of gene transfer into organisms, both plant and animal. Investigators have attempted to produce pharmaceuticals, chemicals, and biologicals by gene transfer techniques. Even though a gene may have been identified, cloned, and engineered, it is still necessary to introduce the gene into a host cell in which the gene may be expressed.

Foreign genes may be expressed in the host from DNA integrated into the host genome (transgenic organism), or from extrachromosomal pieces of DNA or RNA which are not inherited (through transient expression vectors). A variety of methods have been developed and are currently available for the transformation of various cells with genetic material. The most success has been achieved with dicotyledonous plants with some limited success reported for the monocotyledonous plants. The most highly developed system for higher plants transformation is derived from the tumor-inducing mechanism of the soil bacterium *Agrobacterium tumefaciens*. The Agrobacterium/Ti plasmid system exploits the elements of the Agrobacterium transformation mechanism. Alternative methods for delivering genetic material to plants include the direct incorporation of DNA such as the transformation of plant cell protoplast. Other techniques include microinjection or DNA bombardment.

Transient expression vectors can be introduced directly into the recipient cell, and result in gene expression in a short period of time, generally 24–48 hours. Viral vectors (both DNA and RNA) offer possibilities as plant and animal transformation vectors. Viral vectors have some advantages over vectors involving non-viral DNA in certain circumstances. Advantages of viral vectors include improvements in the ease of gene introduction.

Viruses that have been shown to be useful for the transformation of plant hosts include caulimovirus (CaMV), tobacco mosaic virus (TMV) and brome mosaic virus (BMV). Transformation of plants using plant viruses is described in U.S. Pat. No. 4,855,237 (bean golden mosaic virus), EP-A 67,553 (TMV), Japanese Published Application No. 63-14693 (TMV), EPA 194,809 (BMV), EPA 278,667 (BV), Brisson, N. et al., Met. Enzymol. 118:659 (1986) (CaMV), Guzman et al. Commun. Molec. Biol.: Viral Vectors, Cold Spring Harbor Laboratory, New York, pp. 172–189 (1988), and WO 93/03161 (TMV). Pseudovirus particles for use in expressing foreign DNA in many hosts, including plants, is described in WO 87/06261.

For RNA viruses, a primary consideration is designing a vector that produces infectious transcripts, and therefore preserves the terminal structure of the RNA in order for the transcript to be a good substrate for the viral replicase.

Bacteriophage promoters have proven ideal for directing the synthesis of RNA from DNA clones. One RNA virus expression vector, pPM1, utilized a modified lambda phage $P_r$ promoter. This vector was used to synthesize infectious transcripts of brome mosaic virus (BMV) genomic RNA from BMV cDNA clones. However, most of these viral vectors have not been capable of systemic spread in the plant and expression of the non-viral foreign genes in the majority of the plant cells in the whole plant. Another disadvantage of many of the prior art viral vectors is that they are not stable for the maintenance of non-viral foreign genes. The use of RNA vectors has also been limited by the instability of inserted foreign sequences and disruption of systemic virus spread after replacement of virus genes involved in movement. TMV viral vectors require a subgenomic promoter for operation. The prior art viral vectors do not provide a means for using viral proteases to cleave the foreign proteins made by the transformed plants. Consequently, there is a need for vectors which enable enhanced systemic expression of a nucleic acid sequence after a short inoculation time and for vectors which can be used to produce both native and non-native proteins relative to the host cell, particularly plant cells, while allowing cleavage of the produced protein by viral proteases.

SUMMARY OF THE INVENTION

It is an object of the invention to provide a polyprotein-producing virus expression vector adapted to encoding at least one sequence for at least one heterologous protein. The vector may be used to express heterologous proteins in plants or plant cells.

Accordingly, the present invention provides a viral expression vector encoding for at least one protein non-native to the vector that is released from at least one polyprotein expressed by said vector by proteolytic processing catalyzed by at least one protease in said polyprotein, said vector comprising: (a) at least one promoter; (b) cDNA, wherein said cDNA comprises a cDNA sequence which codes for at least one polyprotein from a polyprotein-producing virus; (c) at least one unique restriction site flanking a 3' terminus of said cDNA; and (d) a cloning vehicle.

The present invention also provides a viral expression vector encoding for at least one protein non-native to the vector that is released from at least one polyprotein expressed by said vector by proteolytic processing catalyzed by at least one protease in said polyprotein, said vector comprising: (a) at least one promoter; (b) cDNA, wherein said cDNA comprises a cDNA sequence which codes for at least one polyprotein from a polyprotein-producing virus, and wherein said polyprotein comprises at least one protein non-native to the vector; (c) at least one unique restriction site flanking a 3' terminus of said cDNA; and (d) a cloning vehicle.

The present invention also provides a method for producing an expression vector encoding for at least one selected protein non-native to the vector that is released from at least one polyprotein expressed by said vector by proteolytic processing catalyzed by proteases in said polyprotein, said method comprising: (a) reverse transcribing a polyprotein-producing RNA into cDNA; (b) introducing at least one unique restriction site flanking a 3' terminus of said cDNA; and (c) inserting said cDNA into a cloning vehicle.

The present invention also provides a method for producing an expression vector, adapted for expressing in a host cell at least one selected protein non-native to the vector that can be released from at least one polyprotein by proteolytic processing catalyzed by proteases in said polyprotein, said method comprising: (a) reverse transcribing a polyprotein-producing RNA into a first cDNA; (b) introducing at least one unique restriction site flanking a 3' terminus of said first cDNA; and (c) inserting into said first cDNA a second cDNA sequence wherein said second cDNA sequence encodes a protein non-native to the vector; and (d) inserting said first and second cDNA into a cloning vehicle.

The present invention also provides a method for expressing at least one protein in a host cell, wherein the protein is non-native to the host cell, said method comprising infecting a host cell susceptible to a polyprotein-producing virus with an expression vector, wherein said vector comprises a cDNA sequence encoding at least one polyprotein, each of said polyprotein comprising at least one protein non-native to the vector and at least one protease, and wherein said protein non-native to the vector is released from said polyprotein by proteolytic processing catalyzed by said protease encoded by said cDNA, and expressing said protein non-native to the vector in said host cell.

These and other advantages of the present invention will become apparent from the following detailed description.

BRIEF DESCRIPTION OF THE DRAWINGS

FIG. 5(A) shows wild-type TEV-HAT as derived from transcription of pTEV7DA. FIG. 5(B) depicts TEV-GUS and deletion variants.

FIG. 8(A) depicts extracts from TEV-HAT, and TEV-7del,. FIG. 8(B) depicts extracts from a mock-inoculated plant, wild-type TEV-HAT, TEV-2del, synthetic RNA transcripts from pTEV7DA-2del,. pTEV7DA-ΔGUS, and pTEV7DA-ΔHC.

DETAILED DESCRIPTION OF THE INVENTION

Figure 1:
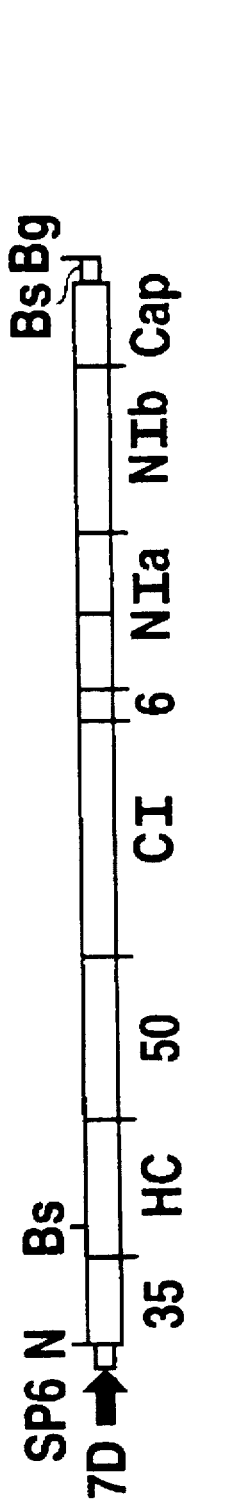
FIG. 1 depicts diagrams of portions of plasmids containing cDNA representing the complete TEV genome and inserted GUS gene.
Figure 1:
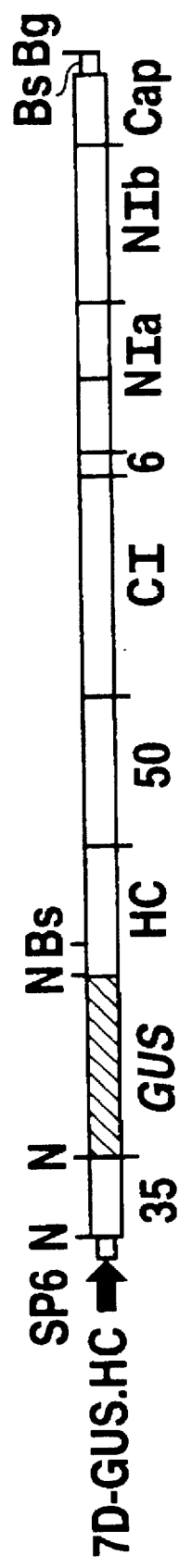
Figure 1:
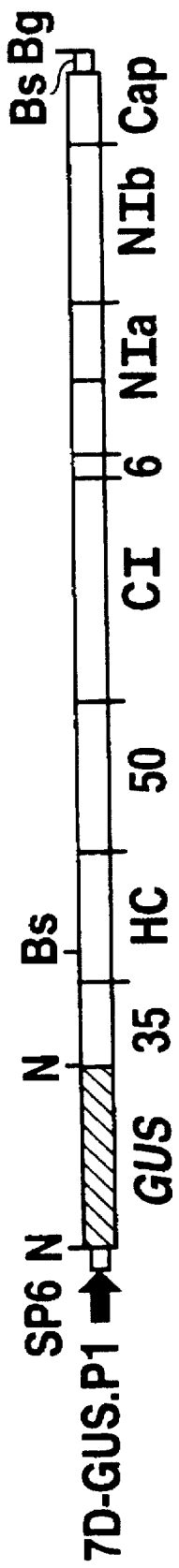

The present invention relates generally to viral vector expression systems for inserting selected genes into host cells. The present invention facilitates the production of selected proteins using a polyprotein-producing virus vector. As used herein, the term "polyprotein-producing virus" means a virus from the picorna-like supergroup as, for example, those described in Dolja, V. V. and Carrington, J. C., Seminars in Virology 3: 315–326 (1992), incorporated herein by reference, which produces a polyprotein. The picorna-like supergroup of viruses encompass both plant and animal viruses. Picorna-like plant viruses are the most preferred. "Polyprotein" means a protein encoded by a virus from the picorna-like supergroup that can be post-translationally cleaved by one or more proteases.

Polyprotein-producing plant viruses include, but are not limited to, potyviruses, nepoviruses, and comoviruses. Potyviruses useful in the present invention include, but are not limited to, tobacco etch potyvirus (TEV), and the viruses referenced in Edwardson, J. R. and Christie, R. G., "The Potyvirus Group: Monograph No. 16 (Agric. Exp. Station, Univ. of Florida, 1991), incorporated by reference herein. Table 1 is a list of the potyviruses taken from the Edwardson and Christie reference that are useful in the present invention. Animal viruses from the picorna-like supergroup that produce polyproteins include, but are not limited to picorna viruses and polio viruses.

TABLE 1

| Potyviruses Useful in the Present Invention | | |
|---|---|---|
| Agropyron Mosaic | Alstroemeria Mosaic | Amaranthus Leaf Mottle |
| Anthoxanthum Mosaic | Aquilegia Virus | Araujia Mosaic |
| Artichoke Latent | Asparagus Virus-1 | Asystasia gangetica Mottle |
| Barley Yellow Mosaic | Bean Common Mosaic | Bean Yellow Mosaic |
| (Pea Mosaic Strain of BYMV) | Bearded Iris Mosaic | Beet Mosaic |
| Bidens Mosaic | Bidens Mottle | Blackeye Cowpea Mosaic |
| Brome Streak Mosaic | Bryonia Mottle | Canavalia maratima |
| Cardamom Mosaic | Carnation Vein Mottle | Carrot Mosaic |
| Carrot Thin Leaf | Cassia Yellow Blotch | Celery Mosaic |
| Celery Yellow Mosaic | Clitoria Mosaic | Clover Yellow Vein |
| (Pea Necrosis strain of CYVV) | Cocksfoot Streak | Colombian Datura |
| Commelina Mosaic | Cowpea Aphid-Borne Mosaic | Crinum Mosaic |
| Croatian Clover | Crocus tomasinianus Virus | Cypripedium calceolus Virus |
| Daphne Virus-Y | Dasheen Mosaic | Datura 437 |
| Datura Mosaic | Datura Shoestring | Dendrobium Mosaic |

TABLE 1-continued

Potyviruses Useful in the Present Invention

| | | |
|---|---|---|
| Desmodium Mosaic | *Dioscorea alata* Ring Mottle | Dioscorea Green Banding |
| *Dioscorea trifida* Virus | Dock Mottling Mosaic | Euphorbia Ringspot |
| *Ficus carica* Virus | Freesia Mosaic | Garlic Yellow Streak |
| Gloriosa Stripe Mosaic | Groundnut Eyespot | Guar Symptomless |
| Guineagrass Mosaic | Habenaria Mosaic | Helinium Virus-Y |
| Henbane Mosaic | Hippeastrum Mosaic | Holcus Streak |
| Hordeum Mosaic | Hungarian *Datura innoxia* Virus | Hyacinth Mosaic |
| Iris fulva Mosaic | Iris Mild Mosaic | Iris Severe Mosaic |
| Isachne Mosaic | Kennedia Virus-Y | Leek Yellow Stripe |
| Lettuce Mosaic | Maclura Mosaic | Malva Vein Clearing |
| Marigold Mottle | Melilotus Mosaic | Mungbean Mosaic |
| Mungbean Mottle | Narcissus Degeneration | Narcissus Late Season Yellows |
| Narcissus Yellow Stripe | Nerine Virus | Nothoscordum Mosaic |
| Oat Mosaic | Oat Necrotic Mottle | Onion Yellow Drawf |
| Ornithogalum Mosaic | Palm Mosaic | Papaya Ringspot |
| Parsnip Mosaic | Passionfruit Ringspot | Passionfruit Woodiness |
| Peanut Green Mottle | Peanut Mild Mottle | Peanut Mosaic |
| Peanut Mottle | Peanut Stripe | Pea Seed-Borne Mosaic |
| Pepper Mild Mosaic | Pepper Mottle | Pepper Severe Mosaic |
| Pepper Veinal Mottle | Perilla Mottle | Plantain Virus-7 |
| Plum Pox | Pokeweed Mosaic | Populus Virus |
| Potato Virus-A | Potato Virus-V | Potato Virus-Y |
| Primula Virus | Reed Canary Mosaic | Rice Necrosis Mosaic |
| Ryegrass Mosaic | Soybean Mosaic | Spartina Mottle |
| Statice Virus-Y | Sugarcane Mosaic Virus | (MDMV strains of SCMV) |
| (SRSV strain of SCMV) | Sunflower Mosaic | Sweet Potato Mild Mottle |
| Sweet Potato Russet Crack | Sweet Potato Virus-A | Tamarillo Mosaic Virus |
| Teasel Mosaic | Tobacco Etch | Tobacco Vein Mottling |
| Tomato (Peru) Mosaic | Tradescantia and Zebrina Virus | Tulip Breaking |
| Turnip Mosaic | Ullucus Mosaic | Vallota Mosaic |
| Watermelon Mosaic Virus-2 | Wheat Spindle Streak Mosaic | Wheat Streak Mosaic |
| Wheat Yellow Mosaic | White Bryony Mosaic | Wild Potato Mosaic |
| Wisteria Vein Mosaic | Zucchini Yellow Fleck | Zucchini Yellow Mosaic |

As used herein the term "vector" refers to a vector produced with a polyprotein-producing plant virus cDNA and a cloning vehicle. In a preferred embodiment, the vector includes a coding sequence non-native to the viral vector inserted between coding sequences of the viral genome. Vectors useful in the present invention generate a non-native protein relative to the virus in the host as part of a polyprotein. Native viral proteases present in the vector cleave the polyprotein into individual proteins. "Protein non-native to the viral vector" or "non-native protein" as used herein means a protein(s) or polypeptide(s) that is not expressed by the wild-type virus. A promoter is a DNA sequence that binds RNA polymerase and facilitates initiation of transcription.

In a preferred embodiment the polyprotein-producing virus is TEV. TEV is a well-characterized potyvirus, and contains a positive-strand RNA genome of 9.5 kilobases (kb) coding for a single, large polyprotein that is processed by three virus-specific proteinases. The nuclear inclusion protein "a" proteinase is involved in the maturation of several replication-associated proteins and capsid protein. The helper component-proteinase (HC-Pro) and 35-kDa proteinase both catalyze cleavage only at their respective C-termnini. The proteolytic domain in each of these proteins is located near the C-terminus. The 35-kDa proteinase and HC-Pro derive from the N-terminal region of the TEV polyprotein.

The different polyprotein-producing viruses have different proteinases, but all are considered to cleave both native and non-native proteins from the respective polyproteins.

The present invention demonstrates that polyprotein-producing virus vectors in general, preferably potyvirus vectors, and most preferably TEV vectors, serve as efficient expression vectors. The theoretical yield of protein products encoded by a polyprotein-producing vector is extremely high because all virus genome-encoded proteins are synthesized in equimolar amounts.

Introduction of the vector into the host results in production of the non-native protein contained on the vector during the course of systemic infection of the recombinant virus. The gene encoding the non-native protein is introduced into the virus genome such that the non-native protein is produced as part of a polyprotein precursor with other native viral proteins. Preferably, the sequence encoding the non-native protein is inserted between coding sequences for native proteins of the viral genome. The sequence encoding the non-native protein must have flanking cleavage sites to facilitate removal of the non-native protein from the polyprotein. The engineering of site-specific cleavage sites recognized by the viral proteinases permits proteolytic release of the non-native protein from the polyprotein. Techniques commonly used in the art to effect site directed mutagenesis may be used. These include, for example, the methods described by Kunkel, T. A., et al., *Methods Enzymol.*, 154:367–382 (1982).

In the case where a plant is used as the host cell, the vector should preferably be aphid transmission-defective to prevent transmission of the recombinant vector to other plants. This is accomplished by inactivation of viral components necessary for insect transmissibility, such as, for example, the HC-Pro proteinase in TEV. Introduction of mutations, such as deletions at sites in the insect-transmissible dependent proteins leads to transmission-defective vectors. Mutations may be generated by techniques known to those skilled in the art.

The method for generating a vector comprises reverse transcription of a polyprotein-producing viral RNA by any reverse transcription method commonly used in the art to produce a cDNA. The cDNA is preferably full length, but partial cDNA may also be used, as long as the cDNA is able to code for a functional polyprotein. Double-stranded DNA (d.s. DNA) is generated from the cDNA using any technique known to those skilled in the art, such as, but not limited to, bacterial DNA polymerase and RNase H. Unique restriction endonuclease sites may be added. The d.s. DNA is digested with a suitable restriction endonuclease and the digest is inserted into a cloning vehicle (which may have at least one unique restriction endonuclease site) such as, but not limited to, a plasmid, cosmid or lambda. Resulting expression vectors are propagated in host cells using techniques known to those skilled in the art.

Unique restriction sites are added to the gene encoding the non-native protein to be inserted into the vector. These restriction sites may code for cleavage at the N- or C-termini of the non-native protein (i.e., at the 5' or 3' end). In one embodiment, restriction sites are generated for cleavage by the 35K (P1) protease to maturate the protein. In an alternative embodiment, sites for cleavage at the C-terminus by NIa protease may be introduced.

The gene coding for a protein non-native to the viral vector is inserted into a specific site on the resulting cloning vehicle using any technique known to those skilled in the art for introducing foreign genes into cloning vehicles. The transcripts may be applied to recipient cells by any technique known to those skilled in the art. These include, but are not limited to, manual application, such as abrasive inoculation, particle bombardment, and/or electroporation.

As used herein, the phrase, "recipient cell" or "host cell" is intended to refer to cells that are susceptible to infection by a polyprotein-producing virus. Species from, for example the Solanaceae, Chenopodiaceae, Leguminosae, Amaranthaceae, Compositae, Campanulaceae, Scrophulariaceae, Convolvulaceae, Lobeliaceae families and others which are known to be infected by potyvirus may be transformed. For example, Table 2 shows the species and Families which are known to be infected by TEV as described by Edwardson, J. R., and Christie, R. G., previously incorporated by reference. Additional species may be found which are also susceptible to TEV infection.

TABLE 2

Species Reported to be Infected by Tobacco Etch Virus

| Species | Families | Species | Families |
|---|---|---|---|
| Alonsoa linearis | Scrophulariaceae | N. caudigera | Solanaceae |
| Amaranthus caudatus | Amaranthaceae | N. clevelandii | Solanaceae |
| Atriplex hortensis | Chenopodiaceae | N. digluta | Solanaceae |
| Beta vulgaris | Chenopodiaceae | N. x edwardsonii | Solanaceae |
| Brachycome iberidifolia | Compositae | N. glauca | Solanaceae |
| Browallia major | Solanaceae | N. glutinosa | Solanaceae |
| B. speciosa | Solanaceae | N. langsdorfii | Solanaceae |
| Callistephus chinensis | Compositae | N. longiflora | Solanaceae |
| Campanula drabifolia | Campanulaceae | N. nudicaulis | Solanaceae |
| Capsicum annuum | Solanaceae | N. paniculata | Solanaceae |
| C. frutescens | Solanaceae | N. pauciflora | Solanaceae |
| C. microcarpum | Solanaceae | N. plumbaginifolia | Solanaceae |
| C. pendulum | Solanaceae | N. raimondii | Solanaceae |
| Cassia occidentalis | Leguminosae | N. repanda | Solanaceae |
| C. tora | Leguminosae | N. rustica | Solanaceae |
| Celosia argentia | Amaranthaceae | N. sanderae | Solanaceae |
| Charieis heterophylla | Compositae | N. solanifolia | Solanaceae |
| Chenopodium album | Chenopodiaceae | N. sylvestris | Solanaceae |
| C. amaranticolor | Chenopodiaceae | N. tabacum | Solanaceae |
| C. foetidum | Chenopodiaceae | N. tomentosa | Solanaceae |
| C. quinoa | Chenopodiaceae | N. trigonophylla | Solanaceae |
| Cirsium vulgare | Compositae | N. undulata | Solanaceae |
| Collinsia bicolor | Scrophulariaceae | Niermbergia hippomanica | Solanaceae |
| C. heterophylla | Scrophulariaceae | Nolana lanceolata | Solanaceae |
| Cuscuta californica | Convolvulaceae | Penstemon grandiflorus | Scrophulariaceae |
| C. lupuliformis | Convolvulaceae | Petunia hybrida | Solanaceae |
| Cymbalaria muralis | Scrophulariaceae | P. violaceae | Solanaceae |
| Datura ferox | Solanaceae | Phacelia campanularia | Hydrophyllaceae |
| D. metel | Solanaceae | P. ciliata | Hydrophyllaceae |
| D. meteloides | Solanaceae | P. grandiflora | Hydrophyllaceae |
| D. stramonium | Solanaceae | P. viscida | Hydrophyllaceae |
| Dimorphotheca aurantiaca | Compositae | P. whitlavia | Hydrophyllaceae |
| D. pluvialis | Compositae | Physalis alkekengi | Solanaceae |
| D. sinuata | Compositae | P. angulata | Solanaceae |
| Emmenanthe penduliflora | Hydrophyllaceae | P. ciliosa | Solanaceae |
| Eupatorium lasseauxii | Compositae | P. floridana | Solanaceae |
| Gamolepis tagetes | Compositae | P. heterophylla | Solanaceae |
| Gomphrena globosa | Amaranthaceae | P. ixocarpa | Solanaceae |
| Gypsophila elegans | Caryophyllaceae | P. peruviana | Solanaceae |
| Helianthus annuus | Compositae | P. pruinosa | Solanaceae |

TABLE 2-continued

Species Reported to be Infected by Tobacco Etch Virus

| Species | Families | Species | Families |
|---|---|---|---|
| *Helipterum humboldtianum* | Compositae | *P. pubescens* | Solanaceae |
| *Hyoscyamus niger* | Solanaceae | *P. subglabrata* | Solanaceae |
| *Indigofera hirsuta* | Leguminosae | *Plantago lanceolata* | Plantaginaceae |
| *Lamium amplexicaule* | Labiatae | *Portulaca oleracea* | Portulacaceae |
| *Linaria bipartita* | Scrophulariaceae | *Primula malacoides* | Primulaceae |
| *L. canadensis* | Scrophulariaceae | *Proboscidea jussieui* | Martynaceae |
| *L. maroccana* | Scrophulariaceae | *Rudbekia amplexicaulis* | Compositae |
| *Lobelia erinus* | Lobeliaceae | *Salpiglosis sinuata* | Solanaceae |
| *L. gracilis* | Lobeliaceae | *Schizanthus pinnatus* | Solanaceae |
| *L. hederacea* | Lobeliaceae | *Senecio vulgaris* | Compositae |
| *L. inflata* | Lobeliaceae | *Silene angelica* | Caryophyllaceae |
| *L. tenuior* | Lobeliaceae | *Solanum aculeatissimum* | Solanaceae |
| *Lycium chinensis* | Solanaceae | *S. capsicastrum* | Solanaceae |
| *Lycopersicon esculentum* | Solanaceae | *S. carolinense* | Solanaceae |
| *L. hirsutum* | Solanaceae | *S. elaegnifolium* | Solanaceae |
| *L. peruvianum* | Solanaceae | *S. integrifolium* | Solanaceae |
| *L. pimpinellifolium* | Solanaceae | *S. melongena* | Solanaceae |
| *Margaranthus solanaceus* | Solanaceae | *S. nigrum* | Solanaceae |
| *Melilotus albus* | Leguminosae | *S. pseudocapsicum* | Solanaceae |
| *M. indicus* | Leguminosae | *S. seaforthianum* | Solanaceae |
| *M. italicus* | Leguminosae | *S. tuberosum* | Solanaceae |
| *M. messanensis* | Leguminosae | *Spinacia oleracea* | Chenopodiaceae |
| *M. officinalis* | Leguminosae | *Tetragonia expansa* | Aizoaceae |
| *M. sulcatus* | Leguminosae | *Torenia fournieri* | Scrophulariaceae |
| *M. wolgicus* | Leguminosae | *Trigonella calliceras* | Leguminosae |
| *Mollugo verticillata* | Aizoaceae | *T. coerulea* | leguminosae |
| *Nemophilia insignis* | Hydrophyllaceae | *T. corniculata* | Leguminosae |
| *N. maculata* | Hydrophyllaceae | *T. cretica* | Leguminosae |
| *N. merziesii* | Hydrophyllaceae | *T. foenum-graecum* | Leguminosae |
| *Nicandra physaloides* | Solanaceae | *Valerianella locusta* | Valeranaceae |
| *Nicotiana acuminata* | Solanaceae | *Verbena canadensis* | Verbenaceae |
| *N. alata* | Solanaceae | *V. hybrida* | Verbenaceae |
| *N. benthamiana* | Solanaceae | *Zaluzianskya villosa* | Scrophulariaceae |
| *N. bigelovii* | Solanaceae | *Zinnia elegans* | Compositae |
| *N. bonariensis* | Solanaceae | | |

Host cells may be in plants, plant cell cultures, animals or animal cell cultures. Cell cultures include any conventional in vitro cell culture such as, but not limited to, roller bottle, agar, and bioreactor techniques. The host cell may be a plant or an animal cell. It is anticipated that vectors having plant polyprotein-producing viral RNA will infect susceptible plant cells, and that vectors having animal polyprotein-producing viral RNA will infect susceptible animal cells, although some plant host cells may be susceptible to animal polyprotein-producing viral RNA, and some animal host cells may be susceptible to plant polyprotein-producing viral RNA. "Cell" as used herein may be a single cell, a plurality of cells, or an organism.

In order to improve the ability to identify transformants, one may desire to employ selectable or screenable marker gene as, or in addition to, the expressible gene of interest. Such genes may encode either a selectable or screenable marker, depending on whether the marker confers a trait which one can select for by chemical means, i.e., through the use of a selective agent such as an herbicide, antibiotic or the like, or whether it is simply a trait that one can identify through observation or testing (e.g., the R-locus trait). Many examples of suitable marker genes are known to the art and can be employed in the practice of the present invention.

Possible selectable markers for use in connection with the present invention include, but are not limited to, a neo gene which codes for kanamycin resistance and can be selected for using kanamycin, G418, etc.; a bar gene which codes for bialaphos resistance, a mutant EPSP synthase gene which encodes glyphosate resistance; etc. Exemplary screenable markers include beta-glucruonidase (GUS), or an R-locus gene, which encodes a product that regulates the production of anthocyanin pigments (red color) in host cells. Included within the terms "selectable" or "screenable marker" genes are also genes which encode a secretable marker whose secretion can be detected as a means of identifying or selecting for transformed host cells. Examples include markers which are able to secrete antigen(s) that can be identified by antibody interaction, or an enzyme(s) which can be detected catalytically.

The choice of the particular foreign DNA segments to be delivered to the recipient host cells will often depend on the purpose of the transformation.

The vector is used to generate proteins of interest that are not native to the virus in a host cell. This includes the production of important proteins or other products for commercial use, such as lipase, melanin, pigments, antibodies, hormones, pharmaceuticals such as, but not limited to, interleukins, EPO, G-CSF, GM-CSF, hPG-CSF, M-CSF, Factor VIII, Factor IX, tPA, hGH, receptors, insulin, vaccines, antibiotics and the like. The coding sequences for proteins that can be used are known in the art or can be obtained by standard sequencing techniques. Alternatively, the vector may be used to produce an enzyme that is able to convert a natural product to a unique product. This includes, for example, the production of secondary metabolites useful as pharmaceuticals. Alternatively, the vector may be used to produce degradative or inhibitory enzymes.

In an alternative embodiment, the vector is used for the transformation of crop plants to add some commercially desirable, agronomically important traits to the plant. Such traits include, but are not limited to, herbicide resistance, increased yields, insect and disease resistance, physical appearance, food content and makeup, etc. For example, one may desire to incorporate one or more genes encoding herbicide resistance. The bar and glyphosate tolerant EPSP synthase genes are good examples. A potential insect resistance gene which can be introduced includes the *Bacillus thuringiensis* crystal toxin gene, which may provide resistance to pests such as lepidopteran or coleopteran.

Genes encoding proteins characterized as having potential insecticidal activity, such as the cowpea trypsin inhibitor (CpTI); may find use as a rootworm deterrent; genes encoding avermectin may prove particularly useful as a corn rootworm deterrent. Furthermore, genes encoding lectins may confer insecticide properties (e.g., barley, wheat germ agglutinin, rice lectins) while others may confer antifungal properties (e.g., hevein or chitinase).

The following examples illustrate the teachings of the present invention and are not intended to limit the scope of the invention. In particular, although the following examples are limited to plant viruses and plant hosts, the present invention also encompasses recombinant picorna-like animal virus vectors and the animal hosts injected by the animal virus.

EXAMPLE 1

This example demonstrates the production of a potyvirus vector containing a GUS marker, as also described in Dolja, V. V., et al., *Proc. Nat'l Acad. Sci.*, 89: 10208–10212 (1992), incorporated by reference herein.

A DNA copy of TEV RNA (ATCC PV-69) was synthesized with reverse transcriptase (SuperScript from GIBCO-BRL) and a primer complementary to 23 nucleotides (nt) preceding the 3'-terminal poly(A) tail of the virus genome. Double-stranded DNA was generated using *Escherichia coli* DNA polymerase I and RNase H, digested with BstEII, and inserted into BstEII-digested pTL7SN.3–0027, which contained sequences representing the 5' and 3' ends of the TEV genome. A unique Bgl II site was engineered immediately after the 25-nt 3' poly(A) tail by site-directed mutagenesis as described by Kunkel, T. A., et al., *Methods Enzymol.*, 154:367–382 (1982), incorporated by reference herein. A longer poly(A) tail (70–75 nt) was incorporated from pBB5995, resulting in pTEV7D. Plasmids were propagated in *E. coli* strain HB101. FIG. 1 depicts diagrams of portions of plasmids containing cDNA representing the complete TEV genome and inserted GUS gene. The noncoding (open boxes) and coding (stippled shading) regions of the TEV genome, the GUS gene (hatched shading), and SP6 RNA polymerase promoter (black arrow) are shown. Vertical lines below maps indicate sequences coding for proteolytic processing sites, whereas selected restriction sites are indicated above maps. Abbreviations as used in this and other Figures are: N, Nco I; Bs, BstEII; Bg, BglII; 35, 35-kDa proteinase; HC, HC-Pro; 50, 50-kDa TEV protein; CI, cylindrical inclusion protein; 6, 6-kDa TEV protein; NIa, nuclear inclusion protein a; NIb, nuclear inclusion protein b; Cap, capsid protein; 7D, pTFEV7D.

Site-directed mutagenesis was used to introduce Nco I sites flanking the 5' and 3' terminal coding sequences of the GUS gene in pTL7SN.3-GUS. The GUS coding region was excised with Nco I and inserted into the Nco I site that was introduced near the beginning of the HC-Pro coding sequence in pTL7SN.3-0627. The GUS gene and adjacent TEV coding sequences from this plasmid were incorporated into pTEV7D, resulting in pTEV7D-GUS.HC (FIG. 1). The (GUS gene was also inserted into the Nco I site that had been introduced previously at the beginning of the 35-kDa protein coding region in pTL7SN.3-0027. The GUS and adjacent TEV sequences from the resulting plasmid were introduced into pTEV7D, yielding pTEV7D-GUS.P1 (FIG. 1).

Transcripts that were capped with 7-methylguanosine(5') triphospho(5')guanosine were synthesized using bacteriophage SP6 RNA polymerase and cesium chloride-purified, Bgl II-linearized plasmid DNA as described by Carrington, J. C., et al., *J. Virol.*, 64:1590–1597 (1990), incorporated by reference herein. The 5' ends of transcripts from pTEV7D and related plasmids contained two additional nonviral nucleotides. Transcription mixtures were diluted with equal volumes (vol) of 10 mM sodium phosphate buffer, pH 7.4, and applied manually onto young tobacco plants (10 µl per leaf, two leaves per plant) with the aid of carborundum. In passage experiments, infected leaves were ground in 10 vol of 10 mM sodium phosphate buffer containing carborundum and applied manually to leaves of healthy plants with a cotton swab.

Fluorometric assays for GUS activity and measurements of protein concentration were conducted as described by Carrington, J. C., et al., *J. Virol.*, 64:1590–1597 (1990), previously incorporated by reference herein. In situ GUS assays were done by using a colorimetric substrate according to Restrepo et al., *Plant Cell*, 2:987–998 (1990), incorporated by reference herein. Tobacco leaves were vacuum infiltrated with the substrate 5-bromo-4-chloro-3-indolyl β-D-glucuronic acid, cyclohexylammonium salt (X-gluc) (1.2 mM) in 0.5 mM potassium ferricyanide/10 mM EDTA. Manual cross-sections of leaf petioles, stems, and roots were placed directly into the substrate solution and photographed under bright-field optics by using a Zeiss photomicroscope. Total SDS-soluble proteins were extracted from leaf tissue by grinding in 7 vol of protein dissociation buffer (0.625M Tris·HCl, pH 6.8/2% SDS/10% 2-mercaptoethanol/10% (vol/vol) glycerol) and subjected to immunoblot analysis with anti-HC-Pro, anti-capsid, or anti-GUS sera by described procedures.

Approximately 27% (15 of 56) of tobacco plants inoculated with capped RNA transcripts derived from pTEV7D became infected. Using the PCR, RNA isolated from progeny virions was shown to contain the sequence corresponding to the Nco I site engineered at the start codon for TEV polyprotein in pTEV7D, demonstrating the transcript-derived origin of infection. Twenty-five percent (16 of 64) and 0% (0 of 16) of plants inoculated with pTEV7D-GUS.HC and pTEV7D-GUS.P1 transcripts, respectively, became infected. Due to the absence of infectivity, pTEV7D-GUS.P1 was not used further. Virion RNA from pTEV7D-GUS.HC transcript-inoculated plants exhibited decreased electrophoretic mobility compared with RNA from wild-type TEV, suggesting that the GUS gene was retained in progeny virus. Plants infected by the modified virus, which will be referred to as TEV-GUS, lacked the vein clearing and etching typical of plants infected by wild-type TEV.

The GUS gene in pTEV7D-GUS.HC was inserted adjacent to the coding sequence for the 35-kDa proteinase autoproteolytic cleavage site at Tyr-304/Ser-305 between the 35-kDa proteinase and HC-Pro. Insertion of GUS into the polyprotein at this position has been shown not to interfere with the 35-kDa proteinase processing activity. Proteolysis by 35-kDa proteinase and HC-Pro at their respective C-termini was predicted to yield a GUS-HC-Pro fusion protein of approximately 119 kDa.

Figure 2:
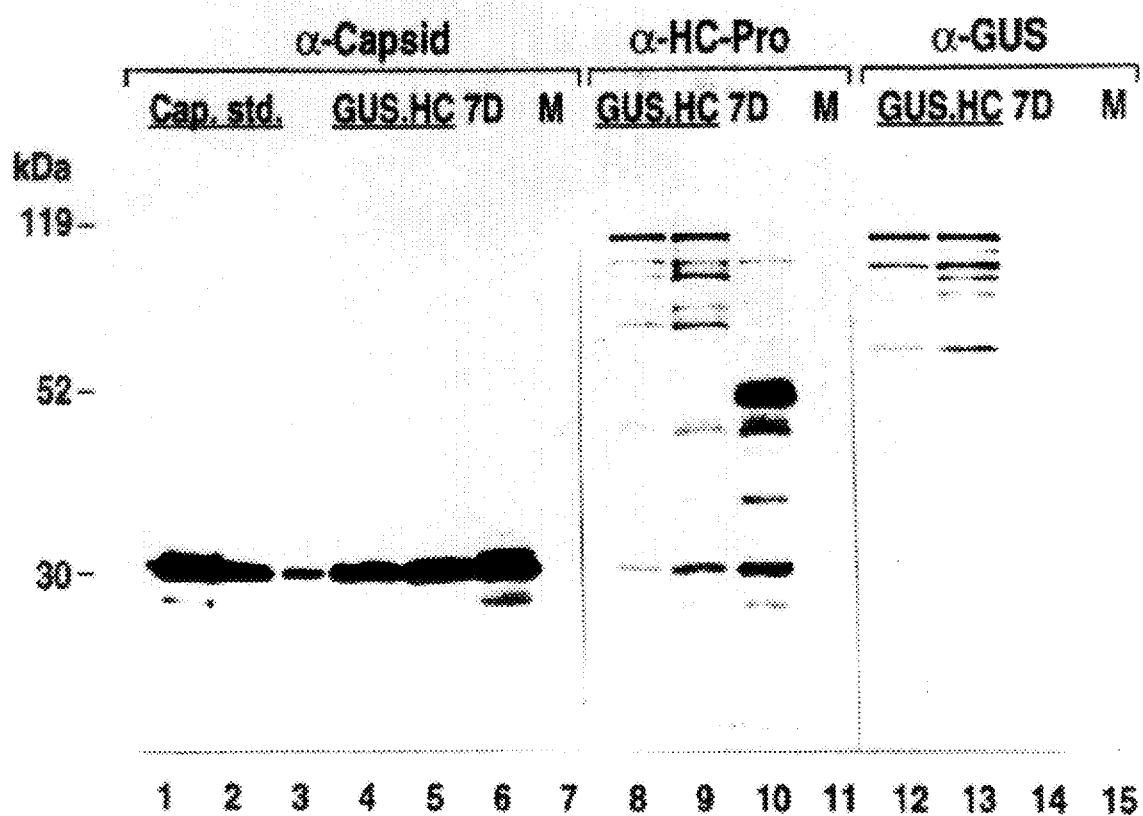
FIG. 2 depicts immunoblot analysis of extracts from RNA transcript-inoculated tobacco plants.

FIG. 2 depicts the immunoblot analysis of extracts from RNA transcript-inoculated tobacco plants. Extracts from pTEV7D (7D; lanes 6, 10, and 14), two pTEV7D-GUS.HC (lanes 4, 5, 8, 9, 12, 13)-infected plants, and a mock-inoculated plant (M; lanes 7, 11, and 15) were analyzed by using anti-capsid protein, anti-HC-Pro, or anti-GUS serum. Lanes 4–15 each contained about 50 μg of SDS-soluble protein. A capsid protein concentration series (capsid standard; Cap. std.) consisting of 1.0 μg, 0.1 μg, and 0.01 μg (lanes 1–3, respectively) was also analyzed. The molecular masses (in kDa) of capsid protein (30 kDa), HC-Pro (52 kDa), and the GUS-HC-Pro fusion protein (119 kDa) are located at left. The minor immunoreactive bands in lanes 8–20, 12, and 13 represent degradation products. Plants inoculated with transcripts from pTEV7D, on the other hand, contained HC-Pro of normal size (52 kDa) that reacted only with anti-HC-Pro serum (lanes 10 and 14). Immunoblot analysis using anti-capsid serum indicated that the levels of capsid protein in plants inoculated with pTEV7D-GUS.HC and pTEV7D transcripts were similar (lanes 4–6). By comparing the level of immunoreactive protein in preparations of known protein concentration against a standard series, capsid protein was shown to account for about 1% of total protein in extracts from plants inoculated with transcripts from either plasmid (lanes 1–6). Immunoblot analysis revealed accumulation of an approximately 119-kDa product that reacted with both anti-HC-Pro and anti-GUS sera (FIG. 2, lanes 8, 9, 12, and 13).

Figure 3:
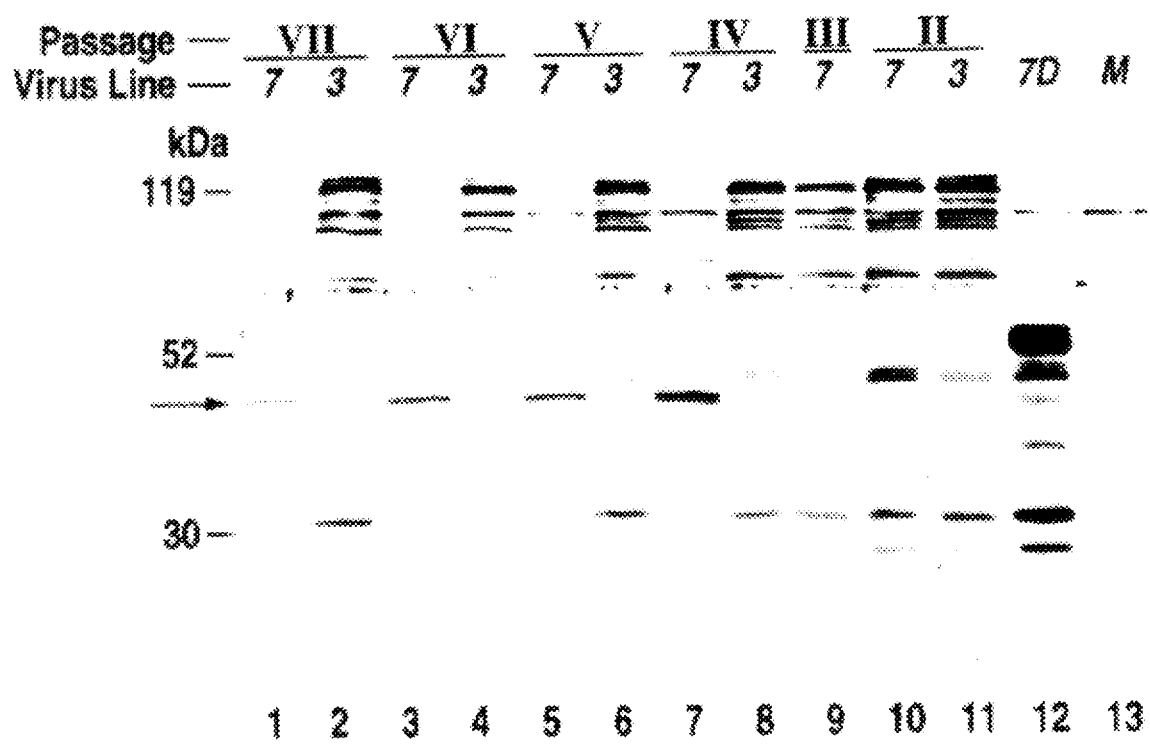
FIG. 3 depicts immunoblot analysis of extracts from tobacco plants infected by serially passaged TEV-GUS.

The stability of the GUS insert within the TEV-GUS genome was assayed by immunoblot analysis in plant-to-plant passage experiments using virus originally recovered from two plants (plant 3 and 7) infected with RNA transcripts. All passages were performed 4–6 days postinoculation (p.i.), except passage II (16 days p.i.). The 119-kDa GUS-HC-Pro protein was intact after seven passages of virus from plant 3 (FIG. 3, lanes 2, 4, 6, 8, and 11), suggesting stable retention of the GUS sequence. In FIG. 3, samples of TEV-GUS were prepared from plants representing two independent virus lineages infected with pTEV7D-GUS.HC RNA transcripts and were analyzed using anti-HC-Pro serum. Extracts from TEV-GUS passages II–VII (lanes 1–11), pTEV7D transcript-inoculated (7D; lane 12), and mock-inoculated (M; lane 13) plants are shown in FIG. 3. By use of a fluorometric assay, GUS activity levels were determined to be comparable in plants from each passage, as well as from an additional seven passages. In contrast, TEV-GUS from plant 7 sustained a deletion in the GUS-HC-Pro coding region that was evident during passage IV, resulting in appearance of an anti-HC-Pro reactive protein that was about 7 kDa smaller than intact HC-Pro (lanes 7, 9, and 10). This form was also detected in the remaining three passages (lanes 1, 3, and 5). The disappearance of the GUS-HC-Pro protein correlated with a loss of GUS activity, as well as a reversion to a mosaic-and etch-inducing phenotype, in plants from passages V–VII.

Figure 4A:
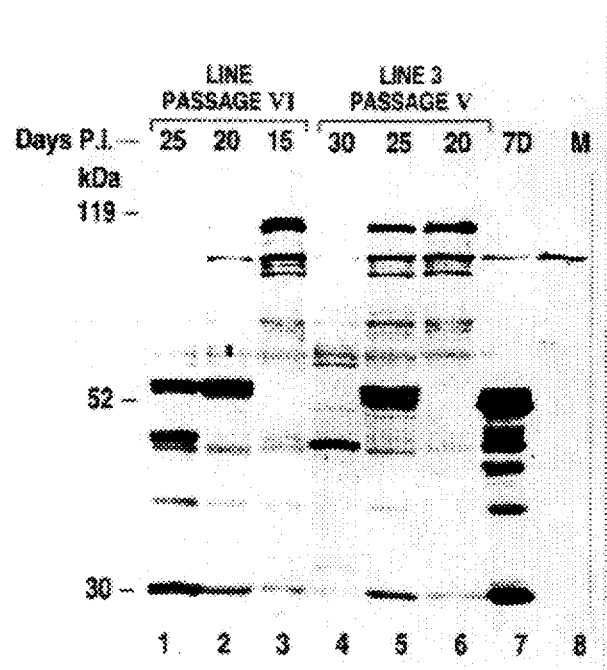
FIG. 4(A) depicts analysis of GUS-HC-Pro fusion protein and GUS activity in aging plants infected by TEV-GUS.
Figure 4B:
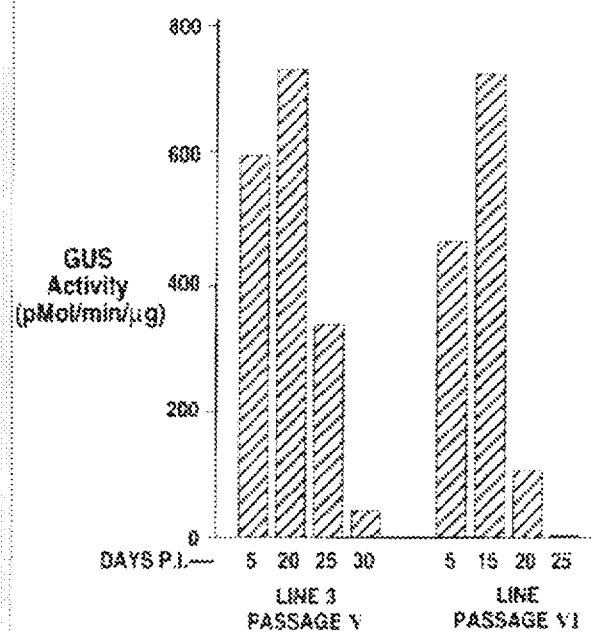
FIG. 4(B) depicts GUS activities as determined by fluorometric assay with the extracts analyzed in FIG. 4(A).
Figure 5A:
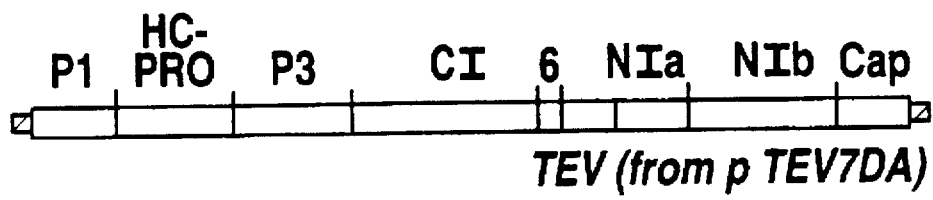
FIGS. 5A–B depict genetic maps of TEV and selected TEV variants used in this study.
Figure 5B:
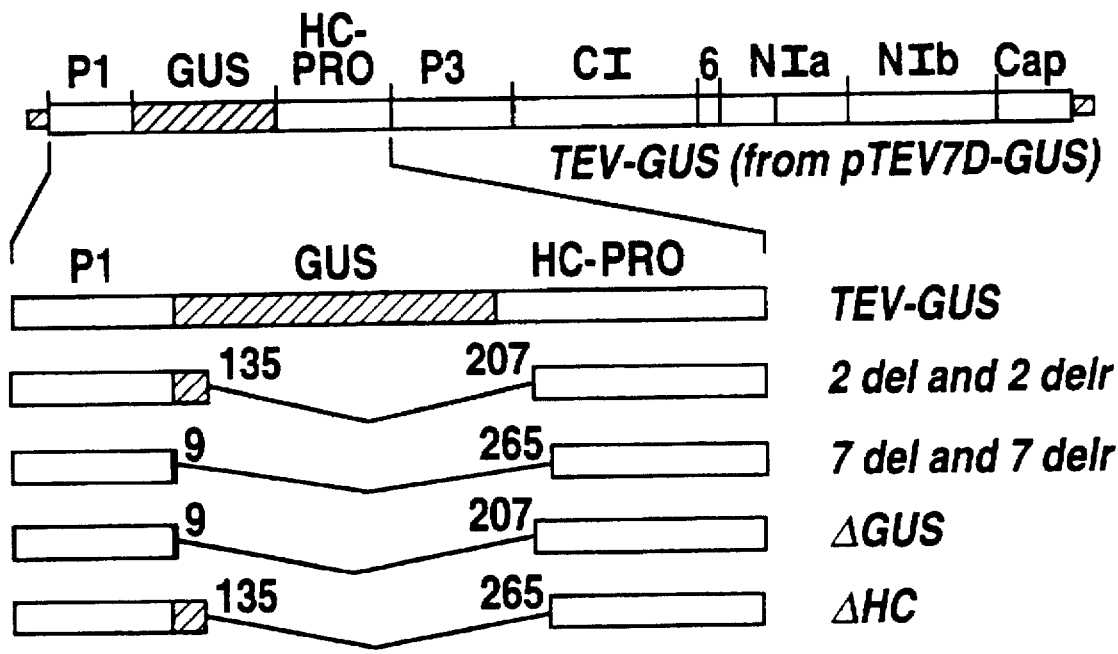

The stability of TEV-GUS as a function of time after inoculation was tested by using virus from passage line 3. Upper systemic leaves from passage V and VI plants were screened for GUS-HC-Pro fusion protein by immunoblot analysis and for GUS activity by using a fluorometric assay at intervals after inoculation. FIG. 4 depicts analysis of GUS-HC-Pro fusion protein and GUS activity in aging plants infected by TEV-GUS. In FIG. 4(A), extracts were prepared at the times p.i. indicated from upper systemic leaves of passage V and VI plants infected by TEV-GUS line 3 and were subjected to immunoblot analysis with anti-HC-Pro serum (lanes 1–6). Extracts were also analyzed from pTEV7D (7D; lane 7) and mock-inoculated (M; lane 8) plants. In FIG. 4(B), GUS activities as determined by fluorometric assay with extracts analyzed in panel A are shown. Deletions that resulted in truncated fusion proteins were detected 20 and 25 days p.i. in passage VI and V plants, respectively (FIG. 4A. lanes 2 and 5, respectively). Additional deletion variants encoding HC-Pro-related proteins smaller than wild-type HC-Pro were evident after an additional 5 days in each plant (lanes 1, 4, and 7). The appearance of deleted forms correlated with decreased amounts of both the intact 119-kDa fusion protein (compare lanes 1 and 2 with lane 3, and lanes 4 and 5 with lane 6) and GUS activity (FIG. 4B).

Plants infected by TEV-GUS were identified in situ localization of GUS activity. Whole leaves were vacuum-infiltrated with the histochemical GUS substrate X-gluc at various times. Plants were innoculated with TEV-GUS at 100 μg/ml. Young tobacco plants were mechanically inoculated with TEV-GUS, and leaves were excised and vacuum-infiltrated with GUS substrate X-gluc at several time points post-inoculation (p.i.). Macroscopic and microscopic visualization of the leaves demonstrated GUS activity. Single infected epidermal cells that contained indigo GUS reaction product were identified 12 hr p.i. on primary inoculated leaves. By 24 hr p.i., movement to adjacent epidermal and mesophyll cells had resulted in infection foci that extended to approximately 10 cells in diameter and that were visible by eye. These foci continued to expand and eventually fused by 96 hr p.i. Measurements of cell-to-cell movement over time indicated that focus expansion occurred at a rate of approximately one cell per 2 hr. Activity of TEV-GUS was detected around segments of vascular tissue in systemically (noninoculated) infected leaves by 60 hr p.i. After 72 hr p.i., virus movement was evident along major and minor veins and into leaf mesophyll cells adjacent to vascular tissue. Spread of virus through mesophyll tissue between veins proceeded at a rate comparable to that measured on inoculated leaves.

To determine which cells or cell types were infected first during systemic spread, cross-sections from stems, roots, and leaf petioles above the site of inoculation were incubated in X-gluc and visualized by light microscopy. This was conducted by in situ localization of GUS activity in cross-sections of petioles, stems, and roots of plants infected by TEV-GUS. Sections were cut by hand at various times p.i. (hr) and incubated with the histochemical substrate X-gluc. No TEV-GUS activity was detected at 24 and 48 hr p.i. in any of the organs. By 72 hr p.i., however, clusters of phloem-associated cells in each of the three organs exhibited activity. Nonphloem-associated cell types, such as xylem parenchyma and cortex, were free of detectable TEV-GUS. Ingress into these cell types was evident after 96 hr p.i.. Strikingly, tissues of lateral roots contained especially high levels of activity.

The TEV-GUS system demonstrated that potyviruses have utility as replicating vectors for the introduction and expression of foreign genes in plants. For TEV, capsid protein accounts for about 1% of SDS-soluble protein in infected leaves (FIG. 2). Unlike most other plant RNA virus vectors, the potyvirus-based system permitted both efficient systemic spread and high insertion capacity.

EXAMPLE 2

This example shows the spontaneous mutagenesis of a plant potyvirus genome after insertion of a foreign gene, as described in Dolja, V. V. et al., *J. Virol.*, 67: 5968–5875 (1993), incorporated by reference herein.

Routine mechanical inoculation of young *Nicotiana tabacum* cv. Xanthi nc plants with wild-type TEV-HAT (high aphid transmissibility) and TEV mutants was performed with the aid of carborundum using homogenates prepared by grinding infected leaves in 2 vol of 10 mM Tris-HCl, 1 mM EDTA, pH 7.6. Homogenates were aliquoted, frozen at −85° C., and thawed prior to inoculation as needed. In some cases, crude virus preparations from individual infected plants were obtained using the same method, but with exclusion of the CsCl-gradient step. Viral RNA was purified using proteinase K digestion, phenol extraction, and ethanol precipitation as described by Carrington, J. C., et al., *Virology*, 139:22–31 (1984), incorporated by reference herein.

Figure 6:
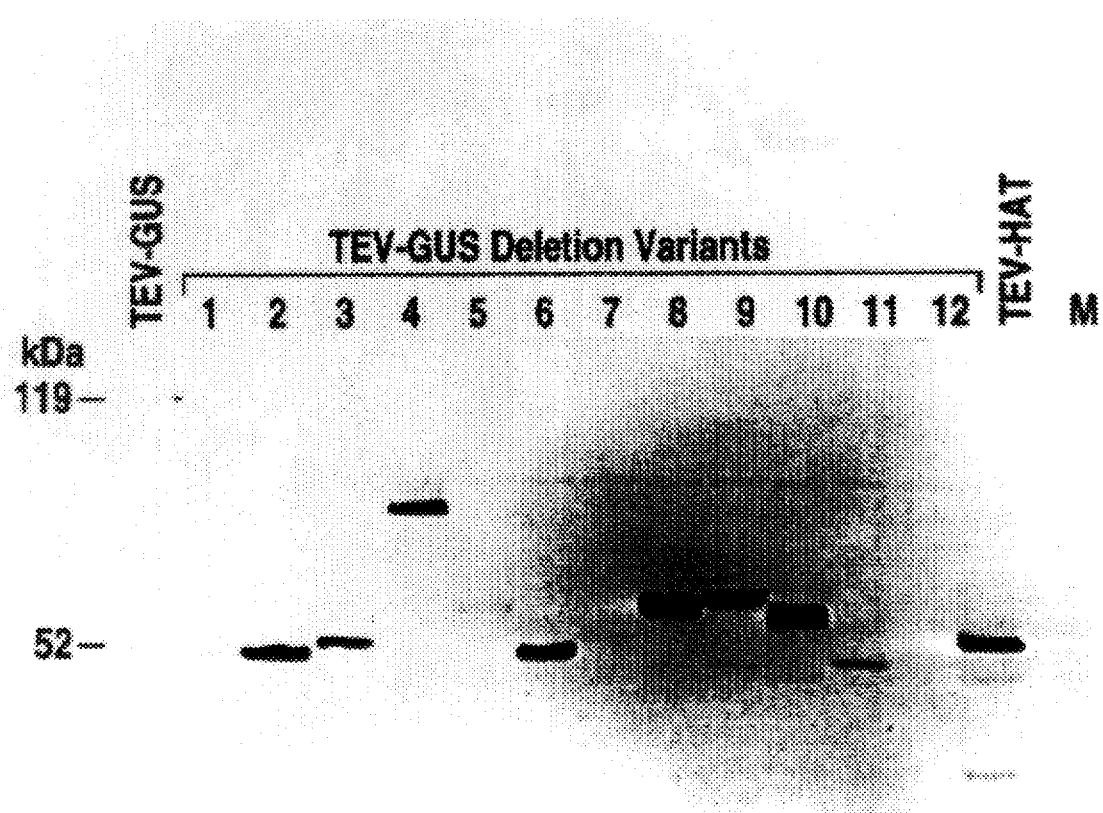
FIG. 6 depicts immunoblot analysis of extracts from upper leaves of TEV-GUS-inoculated tobacco plants using anti-HC-Pro sera.

Complementary DNA spanning the region of deletion in the GUS-HC-Pro coding sequence was obtained by reverse transcription of RNA from crude virus preparations followed by PCR. Reverse transcription and PCR were conducted according to established procedures as described by Kawasaki, E. S., *In PCR Protocols*, pp. 21–27 [Academic Press, Inc., San Diego (1990)], incorporated by reference herein, except that reverse transcriptase buffer from Gibco/BRL was used, rather than PCR buffer in the initial step. The first-strand primer was complementary to TEV nucleotides 1456–1477 within the HC-Pro coding region while the second-strand primer corresponded to nucleotides 781–799 within the P1 region. The first and second-strand primers contained HindIII and BamHI recognition sequences, respectively, to facilitate insertion into the vector pTL7SN. All plasmids were propagated in *E. coli* strain HB101. The sequence of the insert DNA spanning the deletion endpoints in recombinant plasmids was determined using the Sequenase$^R$ kit (U.S. Biochemicals) and a primer corresponding to TEV nucleotides 1015–1032. Each spontaneous deletion variant identified was assigned a code (1del, 2del, etc.).

The sequences between nucleotides 663 to 2416 in the genomes of deletion variants TEV-2del and TEV-7del were reverse transcribed, amplified by PCR, and digested with SnaBI and EcoRI which recognize sites within the P1 and HC-Pro coding regions, respectively. The cleaved PCR fragments were cloned into SnaBI and EcoRI-digested pTL7SN.3-0027DA, which contains sequences corresponding to the 5'-terminal 2681 and 3'-terminal 154 nucleotides of TEV genome. This plasmid was derived from pTL7SN.3-00271) by removal of two nonviral nucleotides separating the 5'-terminus of the TEV sequence from the start site of SP6 RNA polymerase transcription. The resulting plasmids, therefore, possessed the sequences surrounding the deletion breakpoints that were present in TEV-2del and TEV-7del. To generate full-length copies of TEV genomes containing these deletions, the BstEII-BstEII fragment corresponding to TEV nucleotides 1430–9461 was isolated from pTEV7D, and was inserted into BstEII-digested derivatives of pTL7SN.3-0027DA. FIG. 5 depicts genetic maps of TEV and selected TEV variants used in this study. FIG. 5(A) shows wild-type TEV-HAT as derived from transcription of pTFV7DA. The single open reading frame is indicated by the extended, light gray box. Positions encoding polyprotein cleavage sites are shown by the vertical lines. The names of individual proteins are shown above the map. FIG. 5(B) depicts TEV-GUS and deletion variants. TEV-GUS differs from TEV-HAT in that the former contains the coding region for β-glucuronidase (GUS) inserted between the P1 and HC-Pro sequences. The polyprotein encoded by TEV-GUS contains a functional P1 cleavage site between P1 and GUS, resulting in formation of a GUS-HC-Pro fusion protein. The sequences missing in the deletion variants of TEV-GUS are shown in the expanded diagram. The numbers indicate the nucleotide positions of the deletion endpoints in the GUS and HC-Pro coding sequences. Abbreviations as used in this and other Figures are: HC-Pro, helper component-proteinase; CI, cylindrical inclusion protein; NIa, nuclear inclusion protein 'a'; NIb, nuclear inclusion protein 'b'; Cap, capsid protein. These plasmids were named pTEV7DA-2del$_r$ and TEV7DA-7del$_r$ (FIG. 5B). Viruses derived from transcripts of these plasmids were designated TEV-2del$_r$ and TEV-7del$_r$ (the 'r' subscript indicates reconstructed virus). As a control, the same manipulations (reverse transcription, PCR and subcloning) were performed with the wild-type TEV-HAT genome, resulting in plasmid pTEV7DA$_r$.

The deletion mutant TEV-2del (and 2del$_r$) retained nucleotides 1–135 from GUS but lost HC-Pro sequence up to nucleotide 207 (FIG. 5B). Two additional deletion variants were generated by site-directed "loop out" mutagenesis of pTEV7DA-2del$_r$. The GUS sequence between nucleotides 10–135 was removed, resulting in pTEV7DA-ΔGUS. The HC-Pro deletion in pTEV7DA-2del$_r$ was enlarged by removal of sequence corresponding to HC-Pro nucleotides 208–265, yielding pTEV7DA-ΔHC (FIG. 5B).

RNA transcripts capped with $m^7$ GpppG were synthesized using bacteriophage SP6 RNA polymerase (Ambion) and CsCl gradient-purified, BglII-linearized plasmid DNA as described by Carrington, J. C., et al., *J Virol.*, 64:1590–1597 (1990), previously incorporated by reference herein. The undiluted transcription mixtures were applied manually onto leaves of young tobacco plants (10 µl per leaf, two leaves per plant) that were dusted with carborundum.

Total SDS-soluble proteins were extracted from leaf tissue by homogenization in 4 vol of protein dissociation buffer (0.625M Tris-HCl, pH 6.8, 2% SDS, 10% 2-mercaptoethanol, 10% glycerol) and subjected to immunoblot analysis with anti-capsid or anti-HC-Pro sera. Quantitation of capsid protein levels in leaf extracts was conducted using capsid protein standards from purified virus and densitometry of immunoblots with a Model 620 Video Densitometer (Bio-Rad).

Isolation of total RNA from leaf tissue was as described previously by Carrington, J. C., et al., *Virology* 139:22–31 (1984), previously incorporated by reference herein. RNA (5 µg) was denatured by glyoxal treatment, separated by electrophoresis through a 1% agarose gel, and blotted onto a GeneScreenPlus™ membrane (DuPont). Northern hybridization was performed using a randomly-primed, $^{32}$P-labeled probe prepared from a DNA fragment corresponding to TEV nucleotides 1430–9461. The amount of radioactivity bound to each lane was measured using a Beckman LS 5801 Scintillation Counter.

For transmission directly from infected leaves, aphids (*Myzus persicae* Sulz) were allowed a 5–10 min acquisition access period and then transferred to tobacco (*Nicotiana tabacum* cv. Ky 14) seedlings. Ten aphids were placed on each of ten test plants for each treatment in each experiment. In helper component prefeeding experiments, aphids were first allowed a 5–10 min acquisition access period to a concentrated preparation of potato virus Y helper component through a parafilm membrane. Aphids were then transferred to a TEV-infected leaf and processed as described above. Infection of test plants was scored visually.

As demonstrated previously in Example 1, the transfer of TEV-GUS from plant-to-plant at intervals of four to six days resulted in stable retention of the GUS insert over 7 passages. Continuation of this experiment up to 21 passages during approximately 120 days further demonstrated the stability of the foreign insert under these conditions. FIG. 6 depicts immunoblot analysis of extracts from upper leaves of TEV-GUS-inoculated tobacco plants using anti-HC-Pro sera. Each lane contains a sample from an individual plant inoculated with TEV-GUS, TEV-HAT, or buffer (lane M). All plants were propagated 4–5 weeks post-inoculation except the plant labeled TEV-GUS, which was propagated for 6 days post-inoculation. Each of the samples in lanes 1–12 contained a TEV-GUS-derived, spontaneous deletion variant that encoded a truncated GUS-HC-Pro fusion protein. Lanes 4 and 3 contained extracts from plants representing first and second passages, respectively, that derived from a single TEV-GUS-infected plant. Each lane was loaded with equivalent amounts of extract. The weak appearance of HC-Pro-related proteins on lanes 1, 5, 7, and 12 was due to their low yield or rapid turnover. The molecular weights in kilodaltons (kDa) of wild-type HC-Pro and GUS-HC-Pro fusion protein are shown in the Figure. Immunoblot analysis of total protein from the 21st passage plant revealed the full-size, GUS-HC-Pro fusion product (FIG. 6). The level of GUS activity in this plant was comparable to that in plants from the early passages. In contrast, prolonged propagation (3 to 4 weeks) of virtually all TEV-GUS infected plants led to deletion mutants encoding HC-Pro-related proteins that were considerably smaller than GUS-HC-Pro (FIG. 6, lanes 1–12). Several of these variants, all of which were found in systemically infected leaves, expressed HC-Pro forms that were smaller than the wild-type protein (52-kDa), indicating that these mutants contained deletions of GUS and HC-Pro sequences. In some cases, apparent intermediate deletion mutants were identified that, upon further passage, were replaced by variants containing larger deletions (FIG. 6, compare lanes 4 and 3). In control plants infected for five weeks by wild-type TEV-HAT, no deletions of HC-Pro were evident (FIG. 6), suggesting that the deletion phenomenon was specific to TEV carrying the foreign gene.

Virions and corresponding RNA were purified from six individual plants infected by TEV-GUS deletion variants expressing HC-Pro-related proteins of various sizes. The regions overlapping the deletion sites were copied by reverse transcription, amplified by PCR, cloned in a plasmid, and sequenced. Analysis of 40 cDNA clones revealed 9 different deletion variants (Table 3).

TABLE 3

Summary of TEV-GUS deletion mutants.

| Deletion Code[a] | Deletion length (nts) | Deletion 5' end within GUS[b] | Deletion 3' end within HC-Pro[c] | Number of cDNA clones[d] |
|---|---|---|---|---|
| 1del | 1787 | 31(G) | no deletion | 5 |
| 2del | 1890 | 135(T) | 207(G) | 1 |
| 3del | 1828 | 80(A) | 90(A) | 1 |
| 4del | 1939 | 66(T) | 187(G) | 9 |
| 5del | 1741 | 92(A) | 15(C) | 3 |
| 6del | 1789 | 81(T) | 52(T) | 2 |
| 7del | 2074 | 9(T) | 265(C) | 10 |
| 8del | 1804 | 91(G) | 77(C) | 8 |
| 9del | 1840 | 84(G) | 106(A) | 1 |

[a]Variants 4del, 5del, and 6del were isolated from the same plant, as were variants 8del and 9del. All other variants were from individual plants. Note: the numbering of deletions does not correspond to the numbering of lanes in FIG. 6.
[b]Numbering starts with the first nucleotide of the GUS coding sequence. The last GUS-derived nucleotide is shown in parentheses.
[c]Numbering starts with the first nucleotide of the HC-Pro coding sequence, which corresponds to TEV genome nucleotide 1057. The first HC-Pro-derived nucleotide is shown in parentheses.
[d]Number of plasmids sequenced after cloning of PCR products.

The deletions ranged from 1741 to 2074 nucleotides in length, showing almost complete loss of the GUS gene in all mutants. Each mutant, however, retained a short segment of between 9 and 135 nucleotides from the 5' end of the GUS sequence. All but one of the variants also was lacking between 15 and 265 nucleotides from the 5' terminal region of the HC-Pro coding sequence. Interestingly, in no case were the 5' and 3' deletion endpoints entirely within the GUS coding region. All deletions that were mapped resulted in preservation of the open reading frame, and in some examples, led to the formation of new hybrid codons at the junction sites. Two of the six plants analyzed contained multiple deletion mutants, although in both instances one type predominated among the population recovered (Table 3). No mutants contained multiple deletions, nor were non-GUS or non-HC-Pro sequences located at the junctions, suggesting that the deletions were generated by removal of contiguous genome segments.

Figure 7:
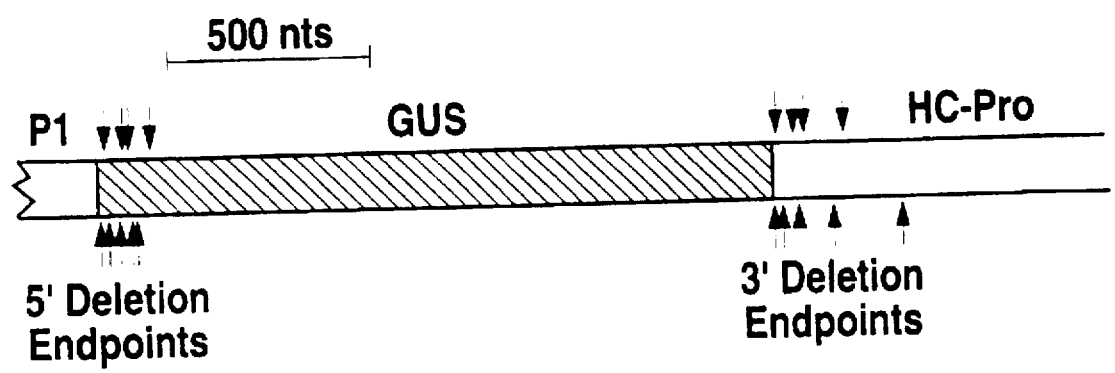
FIG. 7 depicts relative positions of deletion endpoints within the GUS and HC-Pro coding sequences in spontaneous mutants of TEV-GUS.

FIG. 7 depicts relative positions of deletion endpoints within the GUS and HC-Pro coding sequences in spontaneous mutants of TEV-GUS. Each arrow indicates a unique endpoint identified by sequence analysis. The relative positions of the 5' and 3' deletion endpoints are presented diagrammatically in FIG. 7. All of the 5' endpoints clustered within the 130 nucleotide region of GUS gene, whereas the 3' endpoints all mapped to the first 265 nucleotides of the HC-Pro sequence. Alignment of sequences flanking the endpoints of deletions failed to reveal any common elements of primary structure. In fact, the extent of homology of sequences surrounding the junction sites did not exceed two nucleotides in any of the mutants. Similarly, no nucleotide preferences at the deletion endpoints were evident (Table 3).

The fact that the deletion mutants were able to spread systemically suggested that the HC-Pro region lacking in the mutants was not essential for virus replication and intraplant movement. Since it was possible that these plants also contained a low level of nondeleted TEV-GUS providing functions necessary for these processes, uniform virus populations were prepared for the two variants (2del and 7del) containing the largest HC-Pro deletions. An approximately 350 nucleotide segment covering the deletion site in both genomes was amplified by PCR and inserted into pTEV7DA, generating pTEV7DA-2del$_r$ and pTEV7DA-7del$_r$. The resulting constructs harbored the deletion in a wild-type TEV-HAT background and lacked any other sequence changes potentially present in the original mutants. As a control, the corresponding genome segment from wild-type TEV-HAT was amplified and cloned in pTEV7DA to produce pTEV7DA$_r$.

Figure 8A:
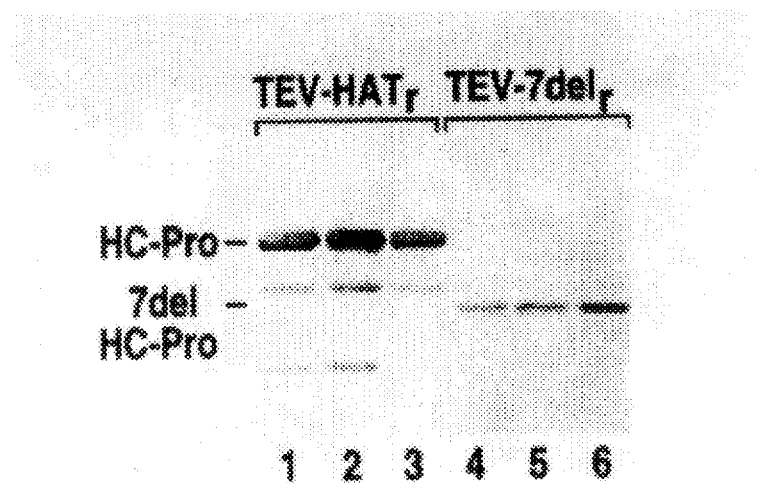
FIGS. 8A–B depict immunoblot analysis with anti-HC-Pro serum of extracts from plants inoculated with synthetic RNA transcripts.
Figure 8B:
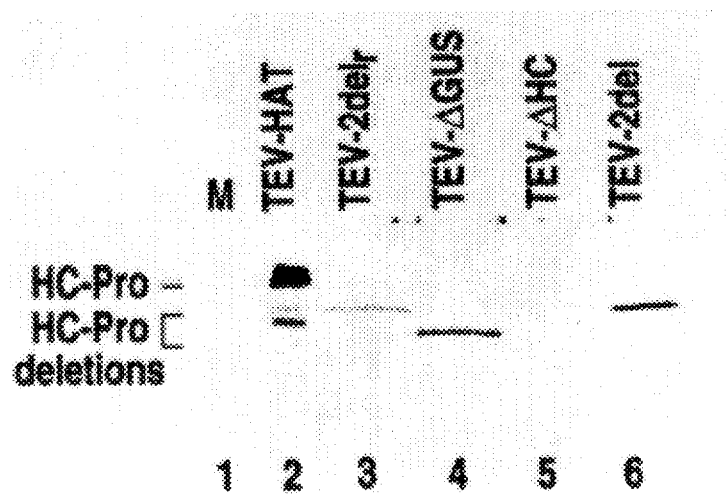

Between 60 and 100% of plants inoculated with synthetic transcripts from pTEV7DA$_r$, pTEV7DA-2del$_r$,and pTEV7DA-7del became infected systemically, demonstrating conclusively that the mutants were capable of replication and movement independent of a non-deleted TEV-GUS. The appearance of systemic symptoms at four days post-inoculation was observed in plants infected by TEV-HAT and the deletion mutants. Systemic symptoms in plants inoculated with TEV-GUS, on the other hand, required five days post-inoculation. FIG. 8 depicts immunoblot analysis with anti-HC-Pro serum of extracts from plants inoculated with synthetic RNA transcripts. FIG. 8(A) depicts extracts which were from systemically infected leaves of three plants inoculated with transcripts from pTEV7DA-HAT$_r$ (lanes 1–3) and three plants inoculated with transcripts from pTEV7DA-7del$_r$ (lanes 4–6). FIG. 8(B) shows extracts from a mock-inoculated plant (lane 1), plants inoculated with virus preparations of wild-type TEV-HAT (lane 2) and TEV-2del (lane 6), or synthetic RNA transcripts from pTEV7DA-2del$_r$ (lane 3), pTEV7DA-ΔGUS (lane 4) and pTEV7DA-ΔHC (lane 5). Each lane was loaded with an equivalent amount of extract. The positions of HC-Pro and truncated HC-Pro derivatives are shown at the left of each panel. Immunoblot analysis using anti-HC-Pro serum indicated that the two reconstructed deletion variants encoded truncated HC-Pro-related proteins, whereas the reconstructed wild-type virus expressed a normal size product (FIG. 8A and 8B, lane 3).

Although the N-terminal HC-Pro sequences clearly were not essential for virus viability, it was noticed that the levels of HC-Pro appeared to be considerably less in plants infected by the mutants compared to wild-type TEV-HAT. Also, the level of GUS-HC-Pro fusion protein in TEV-GUS-infected plants appeared less than HC-Pro in plants infected by TEV-HAT. To determine more precisely the levels of replication of wild-type and mutant viruses in systemically infected tissue, the relative amounts of capsid protein and virus RNA were measured using immunoblot and Northern blot analyses, respectively.

FIG. 9 depicts quantitation of TEV capsid protein (panels A and B) and RNA (panels C and D) present in systemically infected leaves of plants inoculated with wild-type and mutant viruses. Panels 9(A) and 9(B) show capsid protein levels in total protein extracts were determined by reflective densitometry of immunoblots using capsid protein standards from purified virions. Each bar represents the mean (and standard deviation) of three independent samples. Panels 9(C) and 9(D) depict relative viral RNA levels in total RNA extracts determined by measuring radioactivity from a $^{32}$P-labeled probe bound to Northern blots. Two independent samples are shown in each case. For comparative purposes, note that data shown in panels A and C were collected from contemporaneous samples in one experiment, while data in panels B and D were from another set of contemporaneous samples. The insertion of GUS into the viral genome in TEV-GUS decreased the yield of capsid protein and RNA to levels of 15 and 9%, respectively, compared to wild-type (FIG. 9A and C). The presence of GUS, therefore, had a debilitating effect on accumulation of virus. TEV-7del, which specified three amino acid residues from GUS but possessed an HC-Pro deletion to residue 89, yielded even less viral protein and RNA at 8 and 6% of the wild-type levels, respectively (FIG. 9A and C). In contrast, plants infected by TEV-2del, which coded for 45 residues of GUS but lacked 66 HC-Pro residues, accumulated capsid protein and RNA at 25 and 17% of the wild-type levels, respectively (FIG. 9A and C). TEV-2del, therefore, replicated to a degree approximately three times higher than TEV-7del.

Figure 9A:
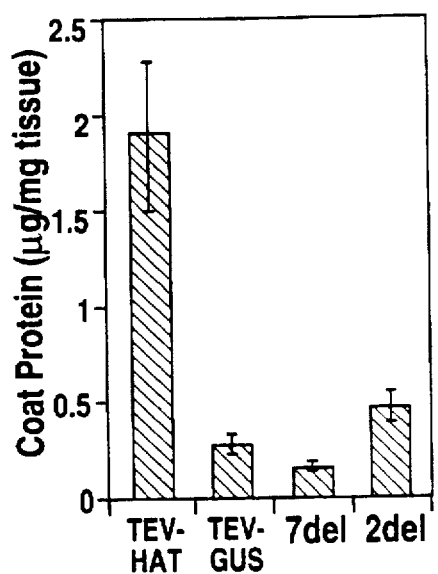
FIGS. 9A–D depict quantitation of TEV capsid protein (A, B) and RNA (C, D) present in systemically infected leaves of plants inoculated with wild-type and mutant viruses.
Figure 9B:
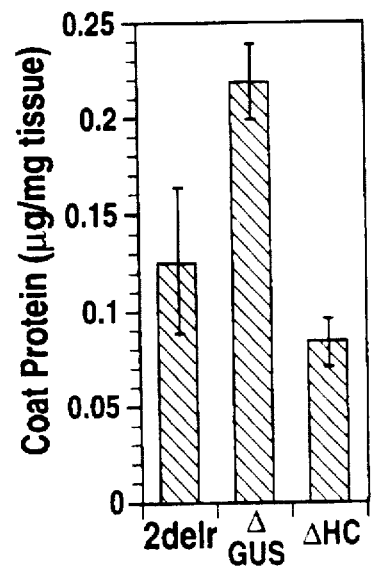
Figure 9C:
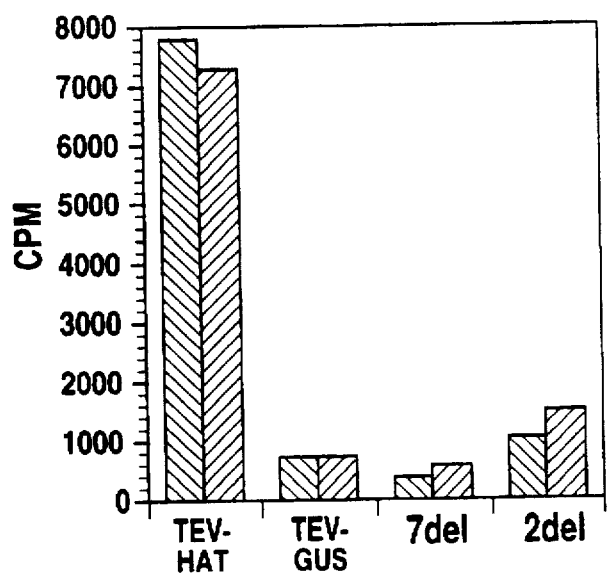
Figure 9D:
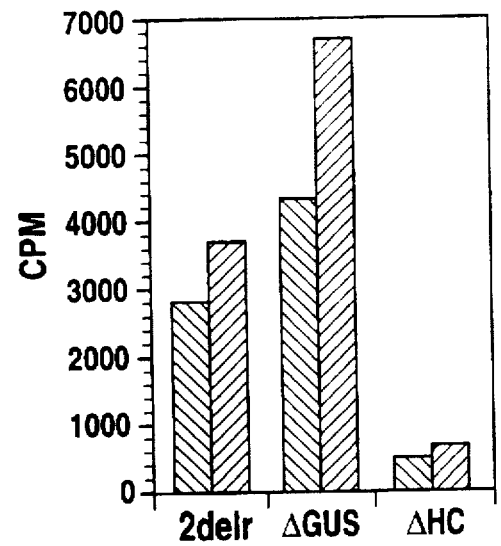

The differences between the two spontaneous mutants may have been due to the presence of the short GUS sequence having a stabilizing effect in TEV-2del, or to the larger deletion within TEV-7del affecting a critical function of HC-Pro. To distinguish between these two possibilities, two site-directed mutations were introduced into pTEV7DA-2del. In the first, pTEV7DA-ΔGUS, the GUS sequence between nucleotides 10–135 was deleted, leaving a short GUS region equivalent to that present in TEV-7del. In the second, pTEV7DA-ΔHC, the HC-Pro deletion was extended from nucleotide 207 to 265, corresponding to the sequence missing in TEV-7del. Immunoblot analysis with HC-Pro-specific antibodies revealed the truncated HC-Pro-related products of the expected sizes in plants inoculated with transcripts from the two mutants (FIG. 8B, lanes 4 and 5). Based on the apparent quantities of HC-Pro deletion products in these plants, TEV-ΔGUS replicated better than TEV-2del, and TEV-ΔHC. This was confirmed by quantitation of the levels of capsid protein and RNA in systemic leaves. Compared to TEV-2del, TEV-ΔGUS directed an average of approximately 70% more capsid protein and RNA, while TEV-ΔHC directed less of these products (FIG. 9B and D). This demonstrated that the presence of the GUS fragment, and the absence of an additional HC-Pro sequence, both conferred a debilitating effect on virus accumulation.

The ability of aphids to transmit TEV-HAT, TEV-GUS, TEV-2del and TEV-7del was tested. Transmission assays demonstrated that only TEV-HAT possessed an aphid-transmissible phenotype (Table 4).

TABLE 4

Aphid transmission of wild-type and mutant TEV variants.

| Virus | Without HC-Pro prefeeding | With HC-Pro prefeeding[a] |
|---|---|---|
| TBV-HAT | 34/40[b] | 10/10 |
| TEV-GUS | 0/40 | 0/20 |
| TEV-2del | 0/30 | 4/30 |
| TEV-7del | 0/30 | 0/20 |

[a]Aphids were allowed access to active HC-Pro from potato virus Y prior to transmission assays.
[b]Data are shown for infected plants/total plants assayed.

The lack of transmission of TEV-GUS, TEV-2del and TEV-7del could have been due to functional defects in the mutant HC-Pro proteins, and/or to the decrease in mutant virus titers and corresponding low concentrations of HC-Pro. Prefeeding of aphids on concentrated preparations of HC-Pro can facilitate transmission of mutant viruses expressing defective HC-Pro proteins. Using highly active preparations of potato virus Y HC-Pro, aphid transmission of TEV-2del was restored, although with low efficiency (Table 4). The inability to transmit TEV-GUS or TEV-7del with the aid of prefeeding was due most likely to low levels of virus accumulation (FIG. 9A, C).

EXAMPLE 3

This is a prophetic example. The gene encoding the sequence for human insulin is inserted into a TEV vector as described for GUS in Example 1. The expression vector is applied manually to plants as in Example 1 to produce human insulin. Human insulin is extracted from the plants.

Many other variations and modifications may be made in the methods herein described, by those having experience in this art, without departing from the concept of the present invention. Accordingly, it should be clearly understood that the methods described in the foregoing description are illustrative only, and not intended as a limitation on the scope of the invention.

We claim:

1. A plasmid comprising:
   (a) at least one promoter;
   (b) cDNA, wherein said cDNA comprises sequences that code for a replicatable genome of a polyprotein-producing potyvirus, and;
   (c) at least one unique restriction site flanking a 3' terminus of said cDNA.

2. A plasmid comprising:
   (a) at least one promoter;
   (b) cDNA, wherein said cDNA comprises sequences that code for a replicatable genome of a polyprotein-producing potyvirus, and wherein said polyprotein comprises at least one protein non-native to the potyvirus, and;
   (c) at least one unique restriction site flanking a 3' terminus of said cDNA.

3. The plasmid according to claim 2 wherein said cDNA sequence for said polyprotein has a coding sequence for said protein non-native to the potyvirus inserted between coding sequences for proteins native to said polyprotein-producing potyvirus.

4. A method for producing a virus, said method comprising:

(a) reverse transcribing a polyprotein-producing potyvirus RNA genome into cDNA;

(b) introducing at least one unique restriction site flanking a 3' terminus of said cDNA;

(c) inserting said cDNA into a cloning vehicle;

(d) producing RNA transcripts from said cDNA using an RNA polymerase; and (e) inoculating plants or plant cells with said RNA transcripts.

5. A method for producing a virus, said method comprising:

(a) reverse transcribing a polyprotein-producing potyvirus RNA genome into a first cDNA;

(b) introducing at least one unique restriction site flanking a 3' terminus of said first cDNA;

(c) inserting into said first cDNA a second cDNA sequence wherein said second cDNA sequence codes for a protein non-native to the potyvirus;

(d) inserting said first and second cDNA into a cloning vehicle;

(e) producing RNA transcripts from said cDNA using an RNA polymerase; and (f) inoculating plants or plant cells with said RNA transcripts.

6. A method for expressing at least one protein in a plant or plant cell, said method comprising infecting a plant or plant cell susceptible to a polyprotein-producing potyvirus with said potyvirus, expressing said potyvirus to produce said polyprotein, wherein said potyvirus codes for at least one protein non-native to the potyvirus and wherein said non-native protein is released from said polyprotein by proteolytic processing.

7. The method according to claim 6 wherein said protein non-native to the potyvirus is a pharmaceutical.

8. The method according to claim 6 wherein said protein non-native to the potyvirus is selected from the group consisting of insulin, hGH, interleukin, EPO, G-CSF, GM-CSF, hPG-CSF, M-CSF, Factor VIII, Factor IX, and tPA.

9. The method according to claim 6 wherein said protein non-native to the potyvirus metabolically interacts with a compound that occurs in the host cell to produce a secondary metabolite of said compound.

* * * * *